United States Patent [19]

Baker, Sr. et al.

[11] Patent Number: 4,552,720

[45] Date of Patent: Nov. 12, 1985

[54] DEBRIS COMPRESSING AUTOCLAVE

[75] Inventors: Richard E. Baker, Sr., Downey; Richard E. Baker, Jr., Santa Ana, both of Calif.

[73] Assignee: American Sterilizer Company, Erie, Pa.

[21] Appl. No.: 577,234

[22] Filed: Feb. 6, 1984

Related U.S. Application Data

[63] Continuation-in-part of Ser. No. 432,241, Jan. 24, 1983, abandoned.

[51] Int. Cl.⁴ .............................................. A61L 2/06
[52] U.S. Cl. ..................................... 422/26; 53/527; 100/73; 422/294
[58] Field of Search .................. 422/26, 27, 28, 294, 422/295, 297, 300; 100/73, 116, 250; 53/511, 512, 527, 528

[56] References Cited

U.S. PATENT DOCUMENTS

| | | | |
|---|---|---|---|
| 2,731,208 | 1/1956 | Dodd | 422/26 X |
| 3,547,577 | 12/1970 | Lovercheck | 422/34 X |
| 3,691,648 | 9/1972 | Kraus | 100/73 X |
| 3,785,281 | 1/1974 | Ligh | 100/116 X |
| 3,808,766 | 5/1974 | Hutchinson et al. | 53/527 X |
| 3,821,927 | 7/1974 | Stratman et al. | 100/73 |
| 3,831,514 | 8/1974 | Jornstrom | 100/70 R |
| 3,861,117 | 1/1975 | De Filippi | 53/528 X |
| 3,926,107 | 12/1975 | Dunlap et al. | 100/73 X |
| 4,004,398 | 1/1977 | Larsson et al. | 53/527 X |
| 4,374,491 | 2/1983 | Stortroen et al. | 422/26 X |
| 4,387,633 | 6/1983 | Ballantyne | 100/116 X |
| 4,455,931 | 6/1984 | Clifford et al. | 100/73 X |

FOREIGN PATENT DOCUMENTS

| | | | |
|---|---|---|---|
| 0031790 | 7/1981 | European Pat. Off. | 422/26 |
| 2505185 | 8/1976 | Fed. Rep. of Germany | 422/26 |
| 1346262 | 2/1974 | United Kingdom | 100/73 |

*Primary Examiner*—Barry S. Richman
*Assistant Examiner*—Brion P. Heaney
*Attorney, Agent, or Firm*—Robert D. Yeager

[57] ABSTRACT

An autoclave for sterilizing used medical equipment and compacting same for disposal comprising a sealable receptacle lined with a thermoplastic liner wherein the liner forms an interior region for receiving used medical equipment. The sealable receptacle is provided with a hydraulic ram for compressing and crushing the equipment contained in a thermoplastic wrap. Thus the medical discards are compressed into portable capsules which then may be discarded in landfills. The hydraulic ram includes controls for automatic cycling of the compression and ejection strokes and the autoclave itself is provided with a steam inlet means through which steam is injected into the liner both to soften the liner and to sterilize the debris before compression. The ram actuation may be coupled to a recorder which records the sterilization temperatures and may include interlocks and clock limits to preclude injury to the operator.

5 Claims, 8 Drawing Figures

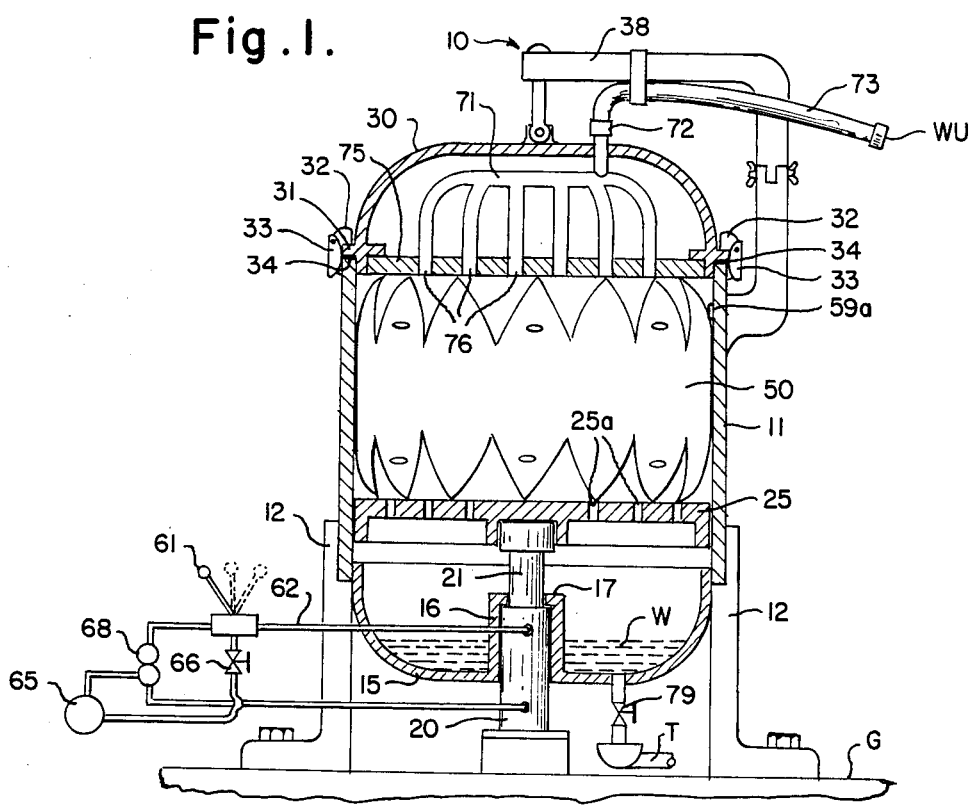

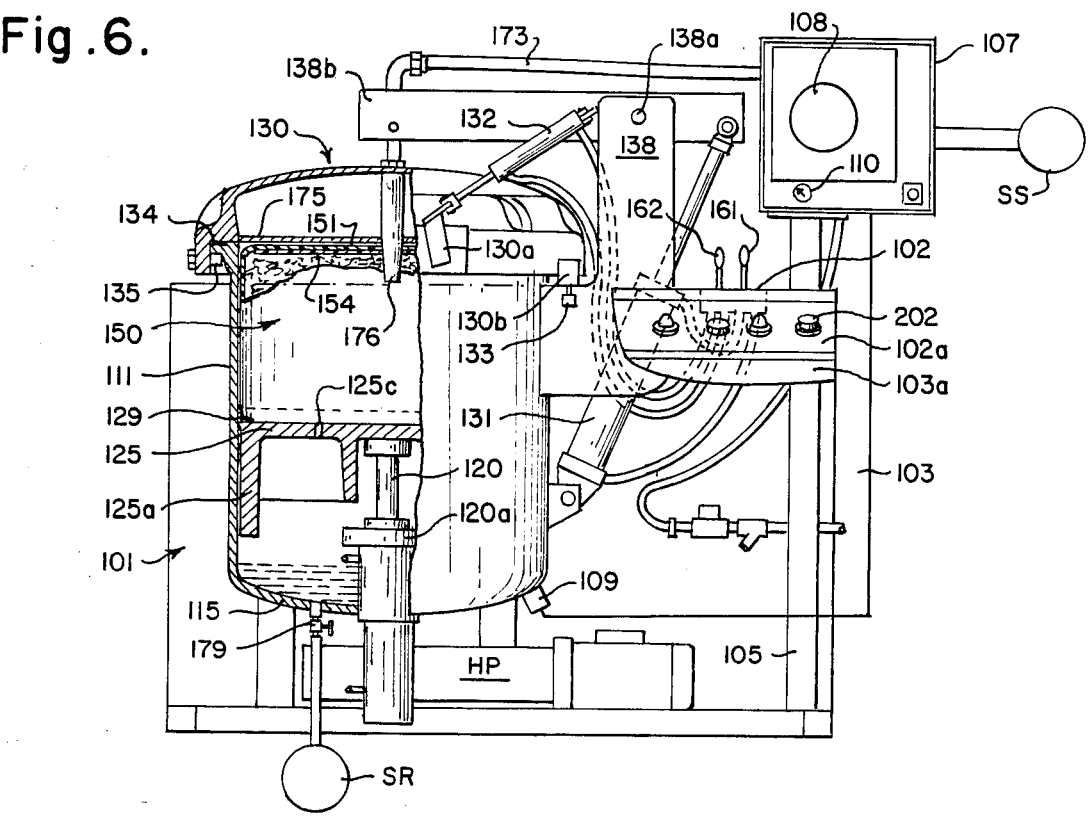
Fig. 6.
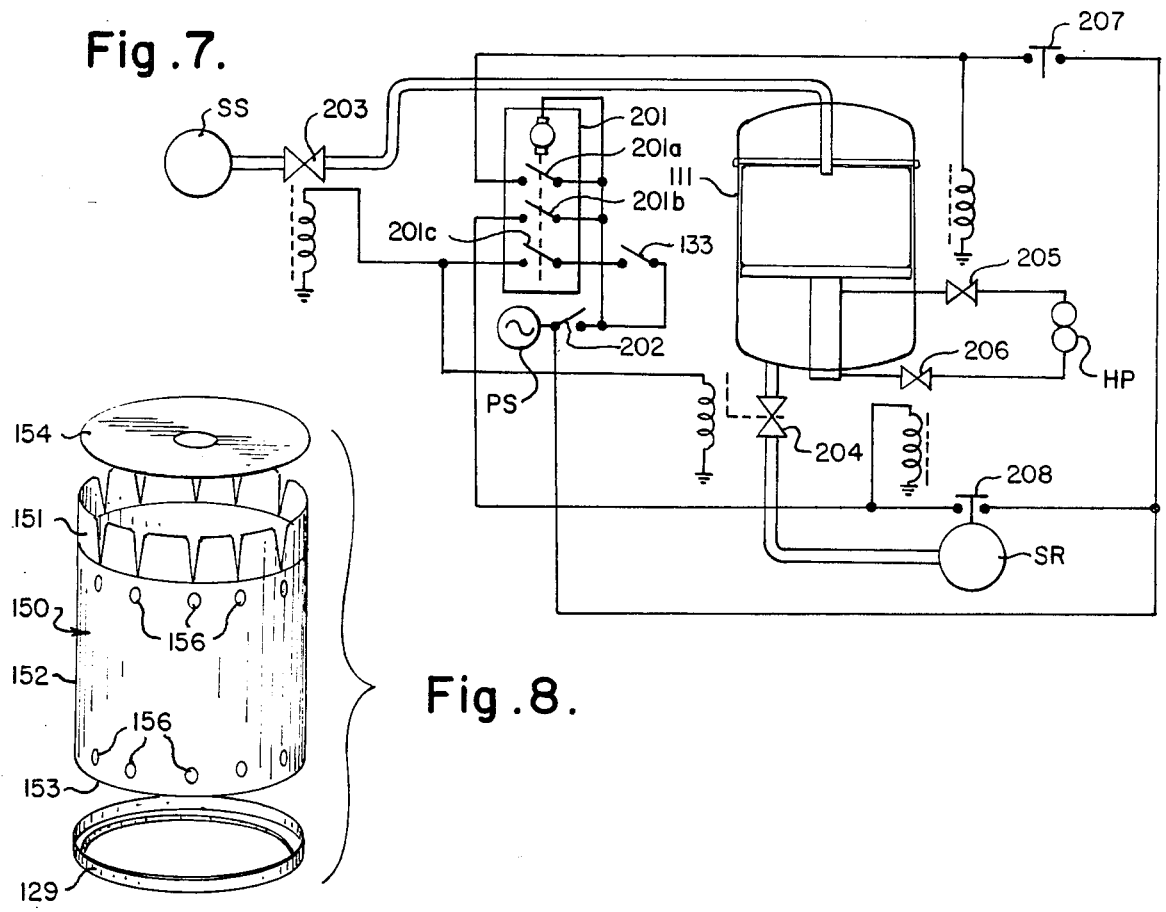
Fig. 7.
Fig. 8.

DEBRIS COMPRESSING AUTOCLAVE

CROSS-REFERENCE TO RELATED APPLICATION

This application is a continuation-in-part of our prior application filed in the U.S. Patent Office on Jan. 24, 1983 and given the Ser. No. 432,241 entitled, "DEBRIS COMPRESSING AUTOCLAVE" now abandoned.

BACKGROUND OF THE INVENTION

1. Field of the Invention

The present invention relates to sterilization devices and more particularly to autoclaves which also compact medical debris.

2. Description of the Prior Art

Autoclaves for sterilizing medical equipment have been known in the past. Recently, however, interest in the community has arisen over the disposal of used medical equipment which although sterilized still presents a public hazard when recovered by those in the illegal drug business. For this reason various statutory schemes have been enacted which require safe disposal. In particular, most statutory schemes require both sterilization and effective destruction of such medical equipment. To meet the foregoing conditions various devices have been developed which in one way or another shred, break or cut the discarded medical equipment which, however, in the course of such function wear out cutting edges or other structural parts. Accordingly, prior art devices like syringe shredders, while suitable for their purpose, often entail repair maintenance sequences which in themselves present a hazard to the maintenance personnel particularly in view of the possible contaminants which sometimes may pass through the sterilization cycle.

Based on these considerations techniques which isolate the hazardous discarded medical devices from those maintaining and operating the sterilization and crushing process have both been sought in the past and are required to meet the various statutory enactments now in effect. It is one such technique that is disclosed herein.

SUMMARY OF THE INVENTION

Accordingly, it is the general purpose and object of the present invention to provide a sterilization system which also includes in the course of the use thereof the sequence of compressing and encapsulating the matter sterilized.

Other objects of the invention are to provide an autoclave adapted to receive a thermoplastic liner and conformed to compress any matter contained in the liner in the course of the sterilization cycle.

Yet additional objects of the invention are to provide an autoclave which also acts as a compactor in the course of use thereof.

Briefly, these and other objects are accomplished within the present invention by providing a substantially cylindrical autoclave housing including a removable top of substantially spherical surface section and a sliding piston deployed within the interior thereof. Formed below the piston, in surrounding relationship about the actuator connected thereto, is a collection trough drained into a disposal line of the hospital. An external steam source is selectively conveyed into a manifold formed in the lid to be passed into the matter deployed for sterilization wrapped in a thermosetting film strip. This strip or liner is formed with the lateral edges thereof convolved to form laterally projecting tongues, the film strip being aligned in a circular fashion within the interior of the autoclave to deploy the tongues on one side thereof onto the piston and to extend the upper tongues into the interior of the lid. Once the liner is thus aligned and heated the piston may then be actuated to compress the bulk debris contained therein against the lid. At the completion of this compression cycle a partial retraction then may be effected, the lid may then be removed followed by a further advancement of the piston to expose the compacted, wrapped mass for removal. In this manner the articles placed into the autoclave for sterilization are both crushed and encapsulated with the result that the subsequent disposition thereof in publically accessible areas will make any retrieval of the used syringes or other articles therein virtually impossible.

Alternatively, the removable top may be provided with a central, downwardly directed spout aligned for insertion into the liner which in this instance may be formed as a cylindrical thermoplastic casing perforated proximate the top and bottom foldovers for circulation and drainage. The spout may then be used to inject the steam into the interior of the liner with the condensate thereof draining down through the aforementioned perforations.

To facilitate the operative sequence of this compressing autoclave timer control may be provided, the timer controlling the injection of steam for a length sufficient to cause sterilization and starting the compression sequence while the liner is still plastic. Moreover, the timed sequence may include lid closure, steam injection, compression, release, opening and presentation all automatically implemented allowing for convenient unattended disposal of the debris. Additionally, the autoclave may be instrumented to provide a permanent record of each disposal cycle, thus providing for vertification of the process.

BRIEF DESCRIPTION OF THE DRAWINGS

FIG. 1 is a side view, in section, of an autoclave constructed according to the present invention;

FIG. 2 is a plan view of a thermosetting liner strip useful with the autoclaves found in FIG. 1;

FIG. 3 is a top view of the autoclave shown in FIG. 1;

FIG. 4 is a side view, once again in section, illustrating the first mode of articulation of the autoclave shown in FIG. 1;

FIG. 5 is yet another side view, in section, illustrating the second mode of articulation of the inventive autoclave;

FIG. 6 is a side view, in partial section, of yet another implementation of the present autoclave;

FIG. 7 is an instrumentation diagram useful with the implementation shown in FIG. 6; and FIG. 8 is yet another illustration of a thermoplastic liner useful with the invention herein.

DESCRIPTION OF THE PREFERRED EMBODIMENTS

As shown in FIG. 1, the inventive autoclave, generally designated by the numeral 10, comprises a tubular section 11 aligned for upright support on a plurality of legs 12 each provided with a fastener hole at the bottom thereof for attachment to ground G. The lower end of the tubular section 11 is attached, through welding or other fastening technique, to a spherical surface 15 aligned to form a dish or collection area at the bottom of the autoclave 10. Surface 15 furthermore includes a central, vertically extending, pipe segment 16 terminating in an inwardly directed flange 17 to which the upper end of a hydraulic actuator 20 is secured. Actuator 20 thus projects within the confines of pipe segment 16 downwardly into the space subjacent surface 15 and extends a piston rod 21 from the confines of pipe segment 16 into the interior of the autoclave. Piston rod 21 at its upper end connects to the underside of a piston 25 conformed for sliding articulation within the interior of the tubular segment 11. Thus, as the hydraulic actuator is rendered operative, translation of the piston 25 through the interior of the autoclave is effected.

At the upper end the inventive autoclave 10 is provided with a lid 30, once again of a substantially spherical section, lid 30 including a peripheral lip 31 about the lower exterior edge thereof conformed to engage the upper end of tubular segment 11. Lid 30 also includes a plurality of latch hooks 32 extending radially therefrom for engagement by a corresponding plurality of over-center latches 33 mounted on the exterior periphery of segment 11.

On the interior lid 30 is provided with a manifold 71 comprising tubing segments joined to a through fitting 72 conveying steam from a wall steam outlet WU. In this form manifold 71 projects downwardly into the interior of the autoclave to pass through openings 76 formed in a compression shield or plate 75. By inserting an elastomeric seal 34 between the lower surface of lip 31 and the upper edge of segment 11 a hermetically closed cavity is formed. Thus any quantity of precipitated water W contained in the annular cavity formed in the bottom surface 15 and the vertical pipe segment 16 may be periodically drained into a trap T through a valve 79. To effect full sterilization steam from manifold 71 passes around the piston 25 and through a plurality of openings 25a formed in the surface thereof into the cavity above the piston to heat and sterilize any particulate matter collected above the piston.

It is contemplated that in the course of the use of the inventive autoclave 10 a thermoplastic liner 50, shown in FIG. 2, be inserted into the cavity above piston 25, thermoplastic liner 50 being conformed as an elongate strip of plastic material sheeting having the lateral edges thereof convolved to form a plurality of tongue-like projections 51. In this form this thermoplastic liner may be wrapped in the manner of a tube and inserted within the interior confines of segment 11, the lower tongues 51 then resting on the upper surface of piston 25. Both the lower and upper tongues 51 extend from corresponding fold lines 58 and 57, each tongue being provided with an opening 56 which at the upper end align with the openings 76 in plate 75. Thus the interior of liner 50 is ventilated for steam sterilizing any matter contained therein. To achieve this alignment the interior of section 11 may include a boss 59a which then engages a hole 59 in the liner indexing the liner with the manifold. Once sufficient debris is collected the hydraulic actuator may then be articulated through the use of a multiposition control handle 61 located on a hydraulic circuit 62 connected across the actuator 20 and pressurized by a hydraulic pump 68. Pump 68, in turn, may be connected to a reservoir of hydraulic fluid 65, which is also connected through a relief valve 66 set to a predetermined operating pressure and selected in one of the positions of handle 61. In this form the articulation of piston 25, according to the illustrations of FIGS. 4 and 5, may take the following sequence:

(a) by selecting a position of handle 61 to communicate with the relief valve 66 a predetermined pressure level is developed within the hydraulic actuator to compress the piston and the debris collected thereabout against the plate 75 to a predetermined pressure. This compression cycle occurs at a time subsequent to the sterilization cycle and thus takes place when the liner 50 and the matter collected therein are heated. The liner material, once heated, begins to crumble and deform in a manner common to most thermoplastic material structures to conform to the shape of the compressed debris.

(b) At this point, handle 61 may be returned to its unpressurized position, removing the pressure force from actuator 20 to allow the removal of lid 30. Lid 30 can then be lifted through a support bracket 38 and transported out of the way. Once this occurs a subsequent articulation of handle 61 will then drive the piston 25 to the limits of its stroke, bringing up the encapsulated and crushed packet for pickup and disposal.

In an alternative implementation, illustrated in FIGS. 6, 7 and 8 the autoclave cylindrical housing 111 is contained within the interior of a rectangular enclosure 101 provided with a top surface 102 mounted on the upper edges of lateral side panels 103 of which the front one 103a is removable for access. Within housing 101 the autoclave housing 111 is attached to a frame 105 which both forms a support base and a vertical stand on which an instrumentation enclosure 107 is mounted above surface 102. This instrumentation enclosure may include a graph plotter 108 recording the temperature sensed by a thermocouple 109 and may further provide pressure gauges 110 monitoring the internal pressures in the autoclave. Moreover enclosure 107 may form the interface between any hospital steam source SS and the autoclave as shall be further set out herein.

In the foregoing configuration the dimensions of enclosure 101 are selected to expose the upper edge of the cylindrical autoclave housing 111 above the surface 102. Additionally, a lateral pivot support arm 138, fixed to one side of housing 111, extends through surface 102 to offer a pivot 138a for a lifting extension 138b. This lifting extension 138b, at one end, connects to the lid assembly 130 and at the other end to the rod end of a lifting hydraulic actuator 131. Concurrently, yet another hydraulic actuator 132 is connected between the lifting extension 138b and a bracket 130a on the periphery of lid assembly 130 and will therefore articulate the lid in rotation about its supporting attachment. Thus the lifting and any rotary motion to affect closure may be hydraulically carried out, the edge of the lid 130 being provided with a trip arm 130b to trip a microswitch 133 upon the completion of the closure stroke.

It should be noted that in this instance the exterior upper edge of housing 111 may include a plurality of cam surfaces 134 exposed to engage rollers 135 extending inwardly from the periphery of lid assembly 130. Accordingly, a positive interlock is hydraulically carried out and sensed by the microswitch 133 to preclude injury to any operator or user. Once closed, and thus interlocked, lid assembly 130 offers an interior opposing surface 175 against which any contained matter is compressed and through which steam may be introduced in a manner set out hereinbelow.

More specifically, housing 111 includes within the interior thereof a compression piston 125 conformed for close sliding fit, piston 125 being mounted on the end of hydraulic actuator 120 extending through the bottom of the housing. This actuator is tied by a flange 120a to the housing bottom surface 115 and the compression stresses are therefore carried within the structure of the housing, the piston 125 being further provided with a peripheral skirt 125a to oppose any torque loading in the course of compression.

In this configuration housing 111 is conformed to receive a bag-like liner 150 having a bottom surface 153 of a platform like that of piston 125 and a lateral surface 152 provided with flaps 151 at its upper edge. An annular plastic insert 154 is receivable in the upper opening of the liner, the flaps 151 being conformed to fold over the periphery thereof. These flaps when folded inwardly over the insert define a central opening through which a steam injecting nozzle 176 extends centrally from the underside of lid assembly 130 to pass through compression surface 175 and to project into the liner, the central deployment of the injection nozzle allowing for the rotary closure articulation of the lid as hereinabove described.

Thus, once closed and locked a passageway is formed into the liner interior for conveying steam through the nozzle as received from a flexible conduit 173 supported on lifting extension 138b. Once thus introduced full steam permeation is assured by way of a plurality of ventilation holes 156 formed along the upper and lower edges of the liner, the steam then passes through holes 125c in the piston surface to return conduit 179 connecting to the steam return SR. Thus, the liner and the contents therein are exposed to the steam flow which is maintained for a sufficient duration to effect sterilization. Once thus heated the liner, now in its plastic state, is compressed against the lid, the piston 125 supporting a removable scraper ring 129 to separate the liner from the autoclave surface in the course of this compression stroke. In the course of the compression stroke any articles in the liner are therefore crushed and surrounded by the liner material to form a massive integral pellet for convenient disposal.

The foregoing operations may be automatically sequenced in accordance with the control diagram shown in FIG. 7. As shown in this figure a clock 201 of conventional configuration, effects switch closure of a selection of switches 201a–201c at predetermined points in time following the initiation of the automated cycle by closure of switch 202. Switch 202 is in circuit with the power supply PS and is positioned on a control section 102a of the top panel 102 adjacent two hydraulic control levers 161 and 162 which respectively control the extensions of actuators 131 and 132. Upon the articulation of these levers and the resulting lid closure, microswitch 133 is closed in circuit with switch 202 to pull open a solenoid valve 203 in the steam injection cycle. Concurrently, yet another solenoid valve 204 is opened for draining the steam and any condensate thereof, thus completing the sterilization cycle. This process may continue for a period of sufficient duration for complete sterilization which concurrently heats the liner. At the completion of this period the clock advances to the compression stroke, opening a solenoid valve 205 between a hydraulic pump HP and the extension side of actuator 120. Once compressed, a cooling period of selected duration is effected by a solenoid valve 206. The lid may then be removed exposing the compressed debris which can then be lifted by a manual switch 207 providing an alternate excitation path to the valve 205. Once withdrawn from the autoclave the debris pellet can then be transported to any convenient site while the piston is repositioned by way of a manual switch 208 for the next collection and compression cycle.

Some of the many advantages of the present invention should now be readily apparent. The invention provides a single container structure which both serves as an autoclave and also as a compactor and encapsulator for medical debris which, when loose, could present a hazard when put to unauthorized use. In addition, the foregoing autoclave structure entails relatively loose clearances between the piston 25 and the interior of segment 11, and therefore very little maintenace effort is necessary, there being no shredding operations in the course of this sequence. Of further advantage is the collection feature of the foregoing autoclave wherein any small particulate shreds or parts of the medical tools crushed in the course of compression are collected within the bottom trough or annular cavity formed in the lower surface 15. Since this lower cavity is periodically drained in the course of each operative sequence substantial assurances are provided of full disposal of any remaining debris.

Obviously many modifications and changes may be made to the foregoing description without departing from the spirit of the invention. It is therefore intended that the scope of the invention be determined solely by the claims appended hereto.

What is claimed is:

1. A process for rendering discarded medical articles safe for disposal comprising the steps of:
   providing a sealable receptacle lined with a liner made of thermoplastic material;
   introducing discarded medical articles into said liner;
   injecting steam into said liner to sterilize said medical articles and to soften said liner to a deformable state;
   compressing said sterilized medical articles within said deformable liner to encapsulate them within the thermoplastic material; thereby forming an encapsulated mass; and
   permitting said encapsulated mass to cool, whereby said thermoplastic material of said liner retains the shape brought about by said compression step.

2. Apparatus for rendering discarded medical articles safe for disposal, comprising:
   a sealable receptacle having an interior chamber;
   a thermoplastic liner lining the interior chamber of said sealable receptable said liner thereby forming an interior region for receiving discarded medical articles;
   means for introducing steam into said sealable receptacle; said liner including means for permitting the passage of steam into the interior region to thereby sterilize discarded medical articles disposed therein and to soften said thermoplastic liner to a deformable state;
   means associated with said sealable receptacle for compressing said thermoplastic liner and discarded medical articles disposed therein; and
   control means for activating said compressing means after said liner has become deformable, whereby once said liner and discarded medical articles disposed therein are compressed, said liner conforms to the shape of the so compressed mass of discarded medical articles.

3. Apparatus as recited in claim 2 wherein:

said receptacle and said liner include complementary indexing means for aligning said liner relative to the interior of said receptacle.

4. Apparatus as recited in claim 2 wherein said means for compressing includes:
a hydraulic ram movable within said receptacle between a first position and a second position, said first position occurring in the course of use of said receptacle in a sealed state and the second position occurring with the receptacle in an open state.

5. Apparatus as recited in claim 2 wherein:
said steam introduction means includes at least one pipe projectable into the midst of said interior region formed by said liner for introducing steam directly into said interior region.

* * * * *